(12) United States Patent
Miller et al.

(10) Patent No.: US 8,113,916 B2
(45) Date of Patent: Feb. 14, 2012

(54) STRAIGHTENING AND CENTERLESS GRINDING OF WIRE FOR USE WITH MEDICAL DEVICES

(75) Inventors: Art Miller, Albertville, MN (US); Charles B. Sjostrom, Tonka Bay, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1880 days.

(21) Appl. No.: 10/346,698

(22) Filed: Jan. 17, 2003

(65) Prior Publication Data

US 2004/0142643 A1 Jul. 22, 2004

(51) Int. Cl.
*B24B 1/00* (2006.01)

(52) U.S. Cl. ............... 451/48; 451/49; 451/54

(58) Field of Classification Search ........ 451/48, 451/49, 54, 190, 194, 209, 242, 243, 244, 451/245, 246; 600/433–435, 585; 604/523–533
See application file for complete search history.

(56) References Cited

U.S. PATENT DOCUMENTS

| | | | |
|---|---|---|---|
| 2,107,810 A | 2/1938 | Wherry | |
| 2,495,329 A * | 1/1950 | Hopkins | 451/48 |
| 3,079,741 A * | 3/1963 | Render | 451/49 |
| 4,538,622 A | 9/1985 | Samson et al. | |
| 4,719,924 A | 1/1988 | Crittenden et al. | |
| 4,721,117 A | 1/1988 | Mar et al. | |
| 4,763,647 A | 8/1988 | Gambale | |
| 4,779,628 A | 10/1988 | Machek | |
| 4,811,743 A | 3/1989 | Stevens | |
| 4,846,186 A | 7/1989 | Box et al. | |
| 4,895,168 A | 1/1990 | Machek | |
| 4,991,602 A | 2/1991 | Amplatz et al. | |
| 5,007,434 A | 4/1991 | Doyle et al. | |
| 5,147,317 A | 9/1992 | Shank et al. | |
| 5,178,158 A | 1/1993 | de Toledo | |
| 5,259,393 A | 11/1993 | Corso, Jr. et al. | |
| 5,267,574 A | 12/1993 | Viera et al. | |
| 5,299,580 A | 4/1994 | Atkinson et al. | |
| 5,313,967 A | 5/1994 | Lieber et al. | |
| 5,339,833 A | 8/1994 | Berthiaume et al. | |
| 5,365,943 A | 11/1994 | Jansen | |
| 5,368,049 A | 11/1994 | Raman et al. | |
| 5,402,799 A | 4/1995 | Colon et al. | |
| 5,409,015 A | 4/1995 | Palermo | |
| 5,488,959 A | 2/1996 | Ales | |
| 5,497,783 A | 3/1996 | Urick et al. | |
| 5,497,785 A | 3/1996 | Viera | |
| 5,507,729 A | 4/1996 | Lindenberg et al. | |
| 5,546,948 A | 8/1996 | Hamm et al. | |
| 5,636,642 A | 6/1997 | Palermo | |
| 5,664,580 A | 9/1997 | Erickson et al. | |

(Continued)

FOREIGN PATENT DOCUMENTS

WO WO 98/46804 10/1998

(Continued)

*Primary Examiner* — Timothy V Eley
(74) *Attorney, Agent, or Firm* — Seager, Tufte & Wickhem, LLC

(57) ABSTRACT

The invention includes methods of manufacturing shafts to be used in medical devices. In particular, methods are disclosed to improve straightness and profile of wire used to form guidewires. The wire is preferably twist-straightened with a desired twist orientation, followed by grinding a desired profile on an apparatus having a spin configuration that is aligned in the same direction as the twist orientation.

11 Claims, 3 Drawing Sheets

U.S. PATENT DOCUMENTS

| | | | |
|---|---|---|---|
| 5,673,707 | A | 10/1997 | Chandrasekaran |
| 5,720,300 | A | 2/1998 | Fagan et al. |
| 5,769,796 | A | 6/1998 | Palermo et al. |
| 5,772,609 | A | 6/1998 | Nguyen et al. |
| 5,782,740 | A | 7/1998 | Schneiderman |
| 5,807,279 | A | 9/1998 | Viera |
| 5,827,201 | A | 10/1998 | Samson et al. |
| 5,836,893 | A | 11/1998 | Urick |
| 5,931,819 | A | 8/1999 | Fariabi |
| 5,984,877 | A | 11/1999 | Fleischhacker, Jr. |
| 5,984,878 | A | 11/1999 | Engelson |
| 6,033,720 | A | 3/2000 | Stoltze et al. |
| 6,039,699 | A | 3/2000 | Viera |
| 6,059,738 | A | 5/2000 | Stoltze et al. |
| 6,080,045 | A * | 6/2000 | Pruitt et al. ............. 451/49 |
| 6,106,485 | A | 8/2000 | McMahon |
| 6,132,389 | A | 10/2000 | Cornish et al. |
| 6,139,510 | A | 10/2000 | Palermo |
| 6,142,958 | A | 11/2000 | Hammarstrom et al. |
| 6,168,571 | B1 | 1/2001 | Solar et al. |
| 6,220,939 | B1 * | 4/2001 | Pruitt ............... 451/49 |
| 6,227,938 | B1 | 5/2001 | Cheetham et al. |
| 6,287,292 | B1 | 9/2001 | Fariabi |
| 6,296,616 | B1 | 10/2001 | McMahon |
| 6,312,314 | B2 | 11/2001 | Cheetham et al. |
| 6,348,041 | B1 | 2/2002 | Klint |
| 6,355,016 | B1 | 3/2002 | Bagaoisan et al. |
| 6,375,629 | B1 | 4/2002 | Muni et al. |
| 6,383,146 | B1 | 5/2002 | Klint |
| 6,390,993 | B1 | 5/2002 | Cornish et al. |
| 6,409,683 | B1 | 6/2002 | Fonseca et al. |
| 6,428,489 | B1 | 8/2002 | Jacobsen et al. |
| 6,464,650 | B2 | 10/2002 | Jafari et al. |
| 6,488,637 | B1 | 12/2002 | Eder et al. |
| 6,502,606 | B2 | 1/2003 | Klint |

FOREIGN PATENT DOCUMENTS

| | | |
|---|---|---|
| WO | WO 00/33984 | 6/2000 |

* cited by examiner

US 8,113,916 B2

STRAIGHTENING AND CENTERLESS GRINDING OF WIRE FOR USE WITH MEDICAL DEVICES

FIELD OF THE INVENTION

The present invention relates to improved medical devices and methods of making the same. More particularly, the invention relates to improved methods of grinding an elongate shaft for use in medical devices such as guidewires or core wires in catheters.

BACKGROUND

A wide variety of medical devices have been developed for medical use. Some of these devices include an elongate shaft that has been ground along a portion of its length to give a desired profile. In particular, a common medical device having an elongate shaft is a guidewire. Guidewires are commonly used for intraluminal procedures to provide and define a pathway to a body site for treatment such as intravascular access to a blockage in a coronary artery, access to the biliary tree to sample tissue, or access to cerebral vasculature for treatment of an aneurysm. The guidewire defines and maintains the pathway to the treatment site to allow other treatment devices, such as balloon catheters or stent delivery catheters, to be routed quickly over the guidewire to the treatment site and continues to maintain the pathway during exchange of devices.

Certain balloon catheters also incorporate an elongate shaft as a core wire to provide stiffening over a portion of the catheter's length. The core wire may be ground to include a taper to adjust or change the flexibility in that region.

To be useful for the medical device applications described above, the wire used for form the guidewire or core wire must meet stringent specification with respect to size and straightness. Further, a change in profile may be desired over the wire's length in order to vary the flexibility of the device. Procedures have been developed to improve straightness and to create a desire profile. However, there is a need for improvement in these techniques to achieve tighter control over size, profile, and manufacturing costs.

BRIEF SUMMARY

The invention provides design, material and manufacturing method alternatives for producing wire having desired straightness and profile. In a preferred embodiment, the wire for the shaft is twist-straightened. In at least some embodiments, the medical devices include an elongate shaft that is at least partially ground, for example, adjacent the distal end. Grinding may be accomplished using an appropriate grinding apparatus such as a centerless grinding apparatus. Improved control over profile, both in a constant diameter and in tapered regions, is achieved by aligning the twist orientation of the twisted shaft with the spin direction of the grinding apparatus. These and other desirable features are described in greater detail below.

DETAILED DESCRIPTION

Figure 1:
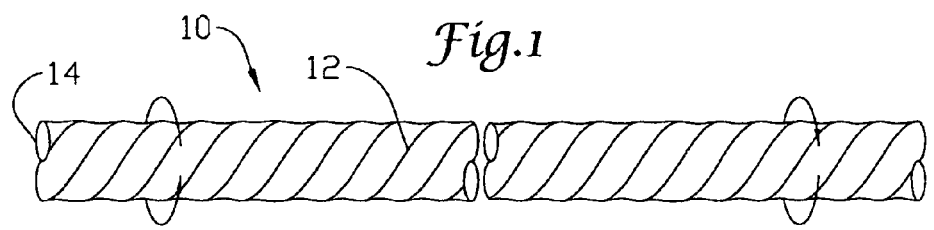
FIG. 1 is plan view of a portion of an elongate shaft that has been twist-straightened.

The following description should be read with reference to the drawings wherein like reference numerals indicate like elements throughout the several views. The detailed description and drawings illustrate example embodiments of the claimed invention.

The manufacturing process of grinding has been used for a number of different purposes and in a number of different industries. For example, portions of a medical device may be ground to precisely control diameter, smooth the transition between adjoining regions, smooth a surface, taper a region, and the like. Due to the precise manufacturing specifications and time required to construct a medical device, the ability to grind precisely, reproducibly and in a time-effective manner is desirable. In at least some embodiments, the invention includes refinements to medical devices and methods of making and/or grinding components thereof.

Turning now to FIG. 1, a medical device may include an elongate shaft 10. In some embodiments, shaft 10 may comprise a generally solid wire. Alternatively, shaft 10 may be generally tubular or include one or more lumens. These embodiments may be used, for example, to form a guidewire, catheter, or other suitable medical device. In preferred embodiments, it is desirable to subject shaft 10 or the wire to be used to form shaft 10 to one or more straightening steps during the construction of a medical device. Some examples of straightening techniques that may be used include passing shaft 10 through a tortuous path, stretching, twist-straightening, and the like. Of these, twist-straightening (axially induced symmetric cold work) is preferred as it imparts desirable benefits in torsional rigidity not achieved in competing processes. Further, processing nitinol wire to be used in a device can require twisting to impart desired properties.

When shaft 10 is twisted, two primary twist orientations are physically possible: left-handed or right-handed. Twisting generally results in a twist-induced "groove" or "flight" (indicated by reference number 12 in FIG. 1) generally disposed between individual turns of shaft 10. These grooves and flights are generally not visible to the naked eye, but can be seen at adequate magnification. Groove 12 traces the outside surface of shaft 10 and wraps in a helical manner about shaft 10. The twist orientation can then be determined in one of two ways. The first is to look at shaft 10 from a side view or longitudinal perspective and observe which direction groove 12 appears to be pointed when following groove 12 from the top to the bottom of shaft 10. If groove 12 "falls" (i.e., when tracing groove 12 from the top to the bottom of shaft 10) to the right, the twist orientation is said to be "right-handed". In contrast, if groove 12 "falls" to the left, the twist orientation is said to be "left-handed". When applying this test to the example shaft 10 shown in FIG. 1, it can be seen that groove 12 falls to the left (from the top of shaft 10 to the bottom of shaft 10) and, thus, shaft 10 has a left-handed twist orientation. It can be appreciated that groove 12 would fall to the right in embodiments of the invention that include the use of shaft 10 having a right-handed twist orientation.

Figure 2:
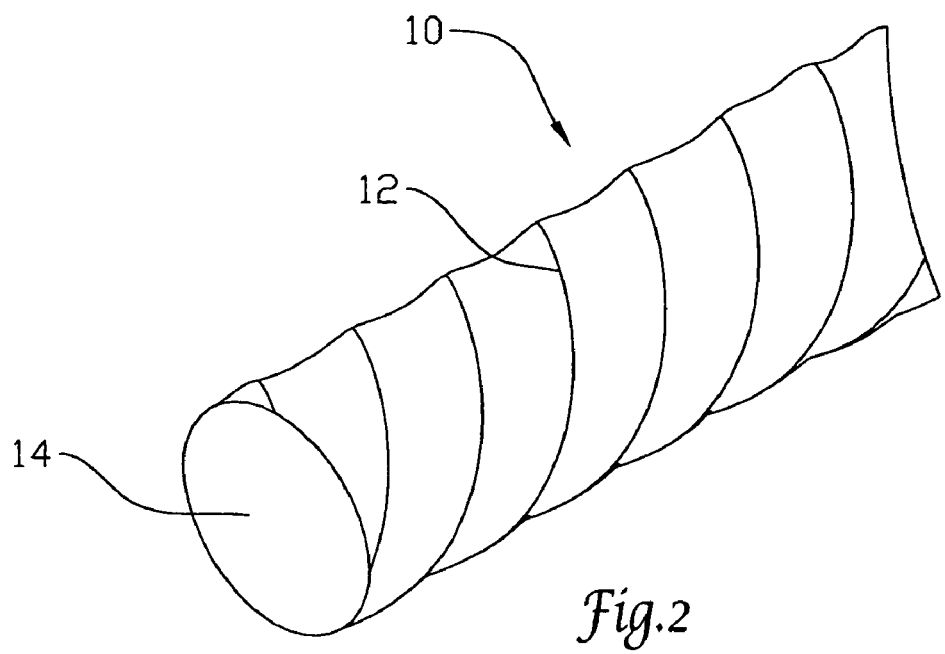
FIG. 2 is a perspective end view of a portion of the elongate shaft of FIG. 1.

Another useful way of determining the twist orientation of shaft 10 is to observe shaft from an end view and then observe the direction (clockwise or counter-clockwise) that groove 12 turns about shaft 10. A view from an end 14 of shaft 10 is shown in FIG. 2. Looking now at groove 12, if the direction that groove 12 turns about shaft 10 is generally clockwise, then the twist orientation is said to be right-handed. In contrast, if groove 12 turns in a counter-clockwise direction, then the twist orientation is said to be left-handed. When applying this test to the example shaft 10 shown in FIG. 2, it can be seen that groove 12 turns in a counter-clockwise direction about shaft 10 and, thus, shaft 10 has a left-handed twist orientation. It can be appreciated that groove 12 would turn about shaft 10 in a clockwise direction in embodiments of the invention that include the use of shaft 10 having a right-handed twist orientation.

Although it may initially appear that the differences between left- and right-handed twist orientations are insignificant or unimportant, it can be appreciated that real structural differences exist between these two orientations. Moreover, one cannot alter the twist orientation by simply changing the perspective from which shaft 10 is viewed, for example by "flipping" shaft 10 lengthwise or 180 degrees. Thus, shaft 10 with a left-handed twist orientation has the same general twist orientation regardless of which side or end that shaft 10 is viewed from. In fact, the left- and right-handed twist orientations are actually non-superimposable mirror images of one another.

A practical illustration of the structural difference between left- and right-handed twist orientations can be realized by considering the manufacturing and use of screws or bolts. Here, the screw has threads that turn about the central axis in a manner similar to how groove 12 turns about shaft 10. The threads of most, typical screws have a right-handed orientation so that the screw can mate with a typical nut or other receiving device. If an otherwise identical second screw with a left-handed orientation is substituted for the first one, the second screw will not be able to mate with the nut. Thus, shaft 10 having a left-handed twist orientation is structurally different from an alternative embodiment of shaft 10 having a right-handed twist orientation in a manner similar to how a left-handed screw is structurally different from a right-handed screw.

In practice, it is common for medical device manufacturers to randomly or non-specifically select the twist orientation of parts when using twist straightening. Frequently, the twist orientation is determined by the unspecified rotation resulting from the electric motor and gearing used to construct the machinery. Additionally, parts having a singular twist orientation may be mixed with one another during the manufacturing process. Thus, "batches" of medical devices are often constructed that manufacture parts derived from a stock of mixed left- and right-handed work pieces. As it will be described in more detail below, it has been found that there are a number of desirable reasons for deliberately choosing a particular twist orientation and manufacturing medical devices from a stock being made of essentially the chosen twist orientation.

As suggested above, it may be desirable to grind or otherwise subject shaft 10 to a number of processing, machining and/or manufacturing steps in order to construct a medical device. For example, a manufacturing step may include (in addition to or as an alternative to grinding) drilling, honing, polishing, burnishing, and the like. Considering now one embodiment where shaft 10 is ground, the grinding step itself can also be thought to have a left- or right-handed orientation. It can be appreciated, however, that the spirit of the invention can be applied to any of the processes or other suitable processes.

Figure 3:
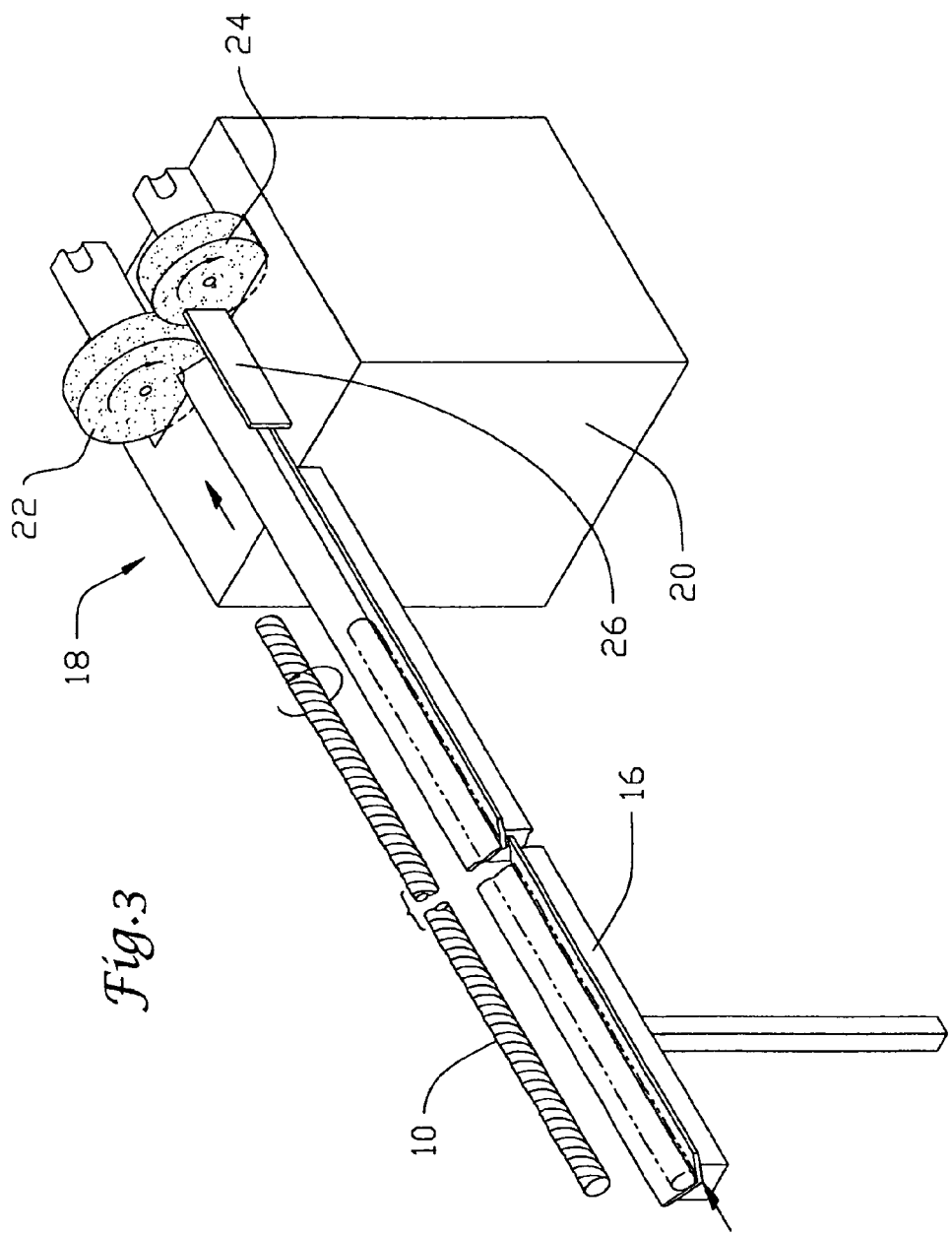
FIG. 3 is a perspective view of a grinding apparatus.

Turning now to FIG. 3, shaft 10 may be placed on the infeed rail 16 of an example centerless grinding apparatus 18. It should be appreciated, however, that any suitable grinding apparatus may be used, for example an O.D. grinding apparatus, or the like, or others. Grinding apparatus 18 can include a base member 20, a work wheel 22, a regulating wheel 24, and a work piece support 26. Although not as intuitively obvious as the twist orientation described above, grinding apparatus 18 can also have a left-handed or right-handed orientation. The convention used to define the orientation of grinding apparatus 18 is described in more detail below. It should be noted that grinding apparatus 18, as shown in FIG. 3, has a left-handed orientation.

In general, the orientation of grinding apparatus 18 (hereinafter spin orientation) is determined by observing the direction and spin of work wheel 22, regulating wheel 24, and shaft 10. As in the case of a left-handed grinding apparatus 18 shown in FIG. 3, from the perspective of shaft 10 the spin of work wheel 22 and regulating wheel 24 are orientated in the clockwise direction as indicated by arrows adjacent each wheel 22/24. It can be appreciated that the direction of wheel 22/24, unlike the twist orientation of shaft 10, is dependent on the perspective from which the spinning is observed. For example, a clockwise spin from the perspective of shaft 10 (i.e., from the side where infeed rail 16 approaches wheels 22/24) would be seen as spinning in the counter-clockwise direction when viewed from the opposite side of base member 20. Therefore, the terms "clockwise" and "counter-clockwise" are meaningful only when provided concurrently with the directional perspective from which they are observing (i.e., from infeed rail 16 side or from the side opposite infeed rail 16). In the following discussion it will generally be assumed that references to the directional spin of wheels 22/24 are from the perspective of the infeed rail 16 side of grinding apparatus 18.

Another component useful in defining the spin orientation of grinding apparatus 18 is the spinning direction of shaft 10 as it approaches and contacts wheels 22/24. As a matter of convention, when shaft 10 approaches clockwise rotating wheels 22/24 (from the infeed rail 16 side), shaft 10 will rotate in the counter-clockwise direction (also from the infeed rail 16 side). The apparent oppositely oriented direction of shaft 10 relative to wheel 22/24 can be reconciled by noting that as shaft 10 encounters work wheel 22, the clockwise spinning of wheel 22 can exert a downward force on the left side of shaft 10. Similarly, the clockwise spinning of wheel 24 can exert an upward force on the right side of shaft 10. Taken together, the forces of wheels 22/24 exerted on shaft 10 will be consistent with shaft 10 spinning in the counter-clockwise direction, from the perspective of the infeed rail 16 side.

The collective spins of wheels 22/24 (being oriented in a clockwise direction from the perspective of infeed rail 16 side) and shaft 10 (being oriented in a counter-clockwise direction from the perspective of the infeed rail 16 side) define grinding apparatus 18 as having a left-handed spin orientation. It can be appreciated that alternative embodiments of grinding apparatus 18 can be configured to have a right-handed spin orientation. In these embodiments, the spin direction of wheels 22/24 would be counter-clockwise and the spin of shaft 10 would be clockwise, both from the perspective of the infeed rail 16 side.

Given that both the twist orientation of shaft 10 and the spin orientation of grinding apparatus 18 both have a directional component or handedness, it can be clearly seen that four distinct combinations are possible: shaft 10 having a left-handed twist orientation being ground by grinding apparatus 18 having a left-handed spin orientation, shaft 10 having a left-handed twist orientation being ground by grinding apparatus 18 having a right-handed spin orientation, shaft 10 having a right-handed twist orientation being ground by grinding apparatus 18 having a left-handed spin orientation, or shaft 10 having a right-handed twist orientation being ground by grinding apparatus 18 having a right-handed spin orientation. It can also be seen that from these four possible configurations, there are two general types of groupings. One is where the twist orientation and the spin orientation both have the same handedness or direction and the other where the twist orientation and the spin orientation have opposite handedness.

Recalling that otherwise identical left- and right-hand twist oriented embodiments of shaft 10 are structurally different, non-superimposable mirror images of each other, it can be appreciated that the structural difference between the embodiments can result in a distinctive interaction between each embodiment of shaft 10 and grinding apparatuses 18 having different spin orientations. For example, consider now the differences between the interactions of either a left- or right-hand twist oriented embodiment of shaft 10 with a left-hand spin oriented grinding apparatus 18. As the left-hand twist oriented embodiment of shaft 10 is spun in the counter-clockwise direction (from the perspective of the infeed rail 16) and is advanced toward and contacts work wheel 22, the tracing of the grinding tends to follow groove 12. Tracing or following groove 12 is understood to mean that as shaft 10 is spun (counter-clockwise) and advanced through grinding apparatus 18, the grinding tends to follow the same path about shaft 10 as groove 12. Thus, the interaction between work wheel 22 and shaft 10 is analogous to the mating relationship between a screw and its proper mating nut. It can be appreciated that a similar interaction occurs between right-hand twist oriented embodiments of shaft 10 and right-hand spin oriented embodiments of grinding apparatus 18.

In contrast, work wheel 22 (of left-hand spin oriented grinding apparatus 18) will not trace or follow groove 12 of a right-hand twist oriented embodiment of shaft 10. Instead, work wheel 22 will tend to grind and drag across grooves 12 and regions between grooves 12. This interaction is analogous to the interaction between a screw and an oppositely oriented nut, similar to trying to cross-thread the screw. It can be appreciated that a similar interaction occurs between left-hand twist oriented embodiments of shaft 10 and right-hand spin oriented embodiments of grinding apparatus 18.

It has been found desirable to configure shaft 10 and grinding apparatus 18 so that the twist orientation and the spin orientation have the same handedness or direction. For example, aligning the spin and twist orientations tends to result in a more consistent, smooth, regular, and predictable grind on shaft 10. In contrast, if the twist and spin orientations are opposite to one another, shaft 10 tends to bounce and feed non-uniformly through grinding apparatus 18. This can result in strain-induced micro-cracking, poor surface finish, accelerated wear on grinding apparatus 18 and components thereof, increased time required to grind, increased manufacturing costs, etc. Micro-cracks, for example, can exacerbate notch sensitivity of certain materials (including nickel-titanium alloys) and can result in low tensile breaks. Aligning the twist orientation and spin orientation can also reduce the internal stresses associated with mechanical working of shaft 10, which can also reduce micro-cracks.

In controlled testing using a left-hand spin oriented grinding apparatus 18, it was determined left-hand twist oriented embodiments of shaft 10 could be ground about 7-33% faster than right-hand twist oriented embodiments of shaft 10. It was also found that the amount of grinding time saved was generally greater when pairing left-hand twist oriented embodiments of shaft 10 ground with left-hand spin oriented grinding apparatuses 18 than when pairing right-hand twist oriented shafts 10 with left-hand spin oriented grinding apparatuses 18. Thus, configuring twist and spin orientation in the same direction can save valuable manufacturing time, which can lower manufacturing costs (for example, up to and in excess of 20%) and lower wear on the machinery used and that these features can be potentiated by using same-handed twist of shafts and spin orientation devices. These findings were replicated in repeat studies that utilized embodiments of shaft 10 that was comprised of differing materials, including those described below. Thus, this feature seems to occur regardless of the material used to manufacture shaft 10.

Similarly, load testing of the various combinations described above demonstrated increased strength in shafts 10 where the twist orientation and spin orientation were aligned relative to oppositely aligned twist and spin orientations. Thus, configuring twist and spin orientation can provide greater consistency in strength, for example by reducing micro-cracks. Again, it was found that the effect of increased strength was potentiated when using left-hand twist oriented embodiments of shaft 10 and left-hand spin oriented embodiments of grinding apparatus 18.

Because the above (and other) features may be desirable when manufacturing a medical device, the present invention generally includes a method of manufacturing medical devices that includes a grinding step and wherein the twist orientation of shaft 10 has the same handedness or direction as the spin orientation of grinding apparatus 18. It can be appreciated that this method can be utilized in the manufacturing of essentially any medical device grinding or similar processes are utilized such as guidewires, catheters (e.g., therapeutic, diagnostic, or guide catheter), endoscopic devices, laproscopic devices, embolic protection devices, orthodontic wires, orthopedic prosthesis components, or any other suitable device.

Figure 4:
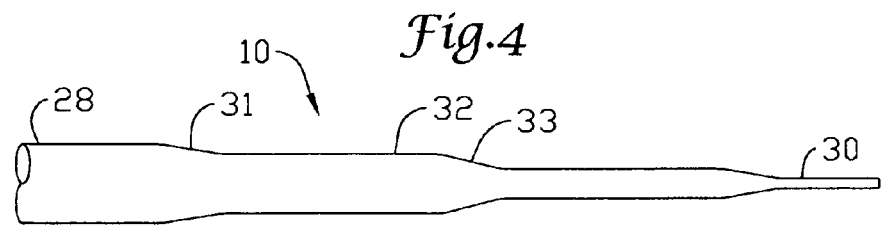
FIG. 4 is a plan view of a portion of an elongate shaft that is at least partially ground to a desired profile.

As depicted in FIG. 4, shaft 10 may include a proximal region 28, a distal region 30, and an intermediate region 32. Each region can be ground to a desired diameter and profile utilizing the methods of the present invention. The shaft can be made of any suitable materials including metals, metal alloys, polymers, or the like, or combinations or mixtures thereof. Some examples of suitable metals and metal alloys include stainless steel, such as 304v stainless steel; nickel-titanium alloy, such as nitinol, nickel-chromium alloy, nickel-chromium-iron alloy, cobalt alloy, or the like; or other suitable material.

Shaft 10, or portions thereof, may also be doped with or otherwise include a radiopaque material. Radiopaque materials are understood to be materials capable of producing a relatively bright image on a fluoroscopy screen or another imaging technique during a medical procedure. This relatively bright image aids the user of the medical device and/or shaft 10 in determining its location. Some examples of radiopaque materials can include, but are not limited to, gold, platinum, palladium, tantalum, tungsten alloy, plastic material loaded with a radiopaque filler, and the like.

The entire shaft 10 can be made of the same material, or in some embodiments, can include portions or sections made of different materials. In some embodiments, the material used to construct shaft 10 is chosen to impart varying flexibility and stiffness characteristics to different portions of shaft 10. For example, proximal region 28 and distal region 30 may be formed of different materials, for example, materials having different moduli of elasticity, resulting in a difference in flexibility. In some embodiments, the material used to construct proximal region 28 can be relatively stiff for pushability and torqueability, and the material used to construct distal region 30 can be relatively flexible by comparison for better lateral trackability and steerability. For example, proximal region 28 can be formed of straightened 304v stainless steel wire or ribbon, and distal region 30 can be formed of a straightened super elastic or linear elastic alloy, for example, a nickel-titanium alloy wire or ribbon.

In embodiments where different portions of shaft 10 are made of different material, the different portions can be connected using any suitable connecting techniques. For example, the different portions of the core wire can be connected using welding, soldering, brazing, adhesive, or the like, or combinations thereof. Additionally, some embodiments can include one or more mechanical connectors or connector assemblies to connect the different portions of the core wire that are made of different materials. The connector may include any structure generally suitable for connecting portions of a medical device. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. patent application Ser. No. 09/972,276, which is incorporated herein by reference.

The length of shaft 10, or the length of individual portions thereof, is typically dictated by the length and flexibility characteristics desired in the final medical device. In some example embodiments, proximal portion 28 may have a length in the range of about 20 to about 300 centimeters and distal portion 30 may have a length in the range of about 3 to about 50 centimeters. It can be appreciated that alterations in the length of shaft 10 or portions thereof can be made without departing from the spirit of the invention. In addition, shaft 10 can have a solid cross-section as shown, but in some embodiments, can have a hollow cross-section. In yet other embodiments, shaft 10 can include a combination of areas having solid cross-sections and hollow cross sections. Moreover, shaft 10, or portions thereof, can be made of rounded wire, flattened ribbon, or other such structures having various cross-sectional geometries. Also, the cross-sectional geometries along the length of shaft 10 can be constant or can vary.

The dimensions and materials used in making shaft 10 are selected based upon the desired application. For instance, a guide catheter is generally characterized as having a multi-layer tubular member construction. This tubular member includes at least a single lumen extending the length of shaft 10. The lumen within the guide catheter possesses an inner diameter capable of receiving a guidewire or another catheter, such as a balloon catheter. Since many catheters have outer diameters in the range of 5F-10F, a guide catheter must either accommodate the largest diagnostic catheter, or identify those catheter sizes the guide catheter may receive. The dimensions of guide catheters are well known in the art.

In at least some embodiments, shaft 10 may include one or more tapered regions 31,33, for example, between proximal region 28, intermediate region 32 and distal region 30, as shown in FIG. 4. According to this embodiment, distal region 30 may be tapered and have an initial outside size or diameter that can be substantially the same as the outside diameter of the proximal region 28, which then tapers to a reduced size or diameter. For example, in some embodiments, the distal region 30 can have an initial outside diameter that is in the range of about 0.010 to about 0.020 inches, that tapers to a diameter in the range of about 0.001 to about 0.005 inches. Tapered regions 31,33 may be linearly tapered, tapered in a curvilinear fashion, uniformly tapered, non-uniformly tapered, or tapered in a step-wise fashion. The angle of any such tapers can vary depending upon the desired flexibility characteristics. The length of the tapers may be selected to obtain a more (longer length) or less (shorter length) gradual transition in stiffness. Although FIG. 4 depicts particular tapered regions, it can be appreciated that essentially any portion of shaft 10 may be tapered and the taper can be in either the proximal or the distal direction. As shown in FIG. 4, tapered region 32 may include one or more portions where the outside diameter is narrowing, for example, the tapered portions, and portions where the outside diameter remains essentially constant, for example, constant diameter portions. The number, arrangement, size, and length of the narrowing and constant diameter portions can be varied to achieve the desired characteristics, such as flexibility and torque transmission characteristics. The narrowing and constant diameter portions as shown in FIG. 4 are not intended to be limiting, and alterations of this arrangement can be made without departing from the spirit of the invention.

The tapered and constant diameter portions of tapered region 31,33 may be formed by any one of a number of different techniques, for example, by the centerless grinding method that is described above. A centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing shaft 10 during the grinding process. In some embodiments, shaft 10 is centerless ground using a Royal Master HI-AC centerless grinder. In at least some embodiments, the spin orientation of the grinding technique is coordinated with the twist orientation of shaft 10 so that both have the same handedness or direction as described above.

Figure 5:
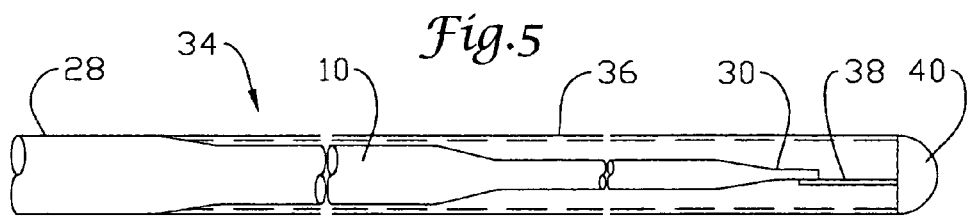
FIG. 5 is a partial cross-sectional view of a distal portion of a guidewire depicting a tapered profile core.

An example medical device 34 is illustrated in FIG. 5 that includes shaft 10 ground according to the methods described above. It can also be seen in FIG. 5 that device 34 may also include an outer member or sheath 36 and a distal shaping ribbon 38 that may extend, for example, from distal region 30 to a distal solder ball tip 40. Sheath 36 may be disposed over at least a portion of shaft 10, for example over distal region 30. Sheath 36 may be made with materials such as polymers, metals, metal alloys, metal-polymer composites, or other suitable materials. Some examples of suitable polymers may include PTFE, fluorinated ethylene propylene (FEP), polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene, Marlex high-density polyethylene, linear low-density polyethylene (for example, REXELL®), polyetheretherketone (PEEK), polyimide (PI), polyetherimide (PEI), other suitable materials, or mixtures, combinations, or copolymers thereof. In some embodiments, sheath 36 can include a liquid crystal polymer (LCP) blended with other polymers to enhance torqueability. By employing selection of materials and processing techniques, thermoplastic, solvent soluble, and thermosetting variants of these and other materials can be employed to achieve the desired results.

In some embodiments, a coating, for example, a lubricious, a hydrophilic, a protective or other type of coating may be applied over portions or all of sheath 36, shaft 10 or other portions of device 34. Hydrophobic coatings, such as fluoropolymers, provide a dry lubricity which improves guidewire handling and device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Figure 6:
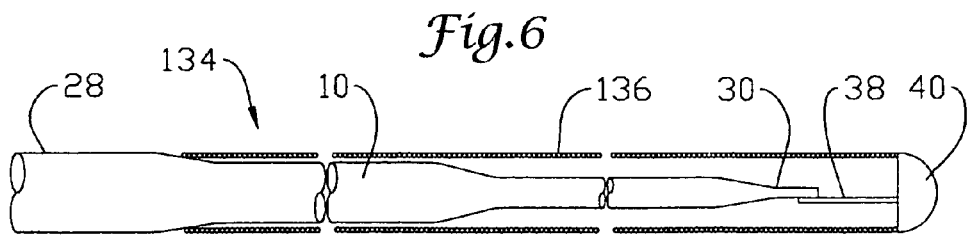
FIG. 6 is a partial cross-sectional view of another example medical device.

FIG. 6 illustrates an alternative medical device 134. Device 134 is essentially the same in form and function as device 34 except that outer member 136 comprises a coil or coiled region. Coil 136 can be disposed about at least a portion of shaft 10. In at least some embodiments, coil 136 is disposed about the shaft 10 such that at least a portion of coil 136 has an inner surface having a size or diameter that is greater than the size or diameter of at least a portion of the outer surface of the elongated shaft 10. For example, coil 136 may be disposed about distal region 30 and can include a portion disposed about one or more of the tapered regions. As such, a space or gap is formed between at least a portion of the coil 136 and at least a portion of the shaft 10.

The coil 136 can be made of any or a variety of suitable materials, including, for example, metals, metal alloys, polymers, metal-polymer composites, and the like. Some examples of materials include stainless steel, nickel-chromium alloy, nickel-chromium-iron alloy, cobalt alloy, platinum, or other suitable materials, and the like. Some additional examples of suitable materials include straightened super elastic or linear elastic alloy (e.g., nickel-titanium) wire, or alternatively, a polymer material, such as a high performance polymer. In some embodiments, coil 136 can be made of, in full or in part, coated with, or doped with a radiopaque material.

Coil 136 may be formed of round wire or flat ribbon ranging in dimensions to achieve the desired characteristics, such as flexibility, and be wrapped in a generally helical fashion by conventional winding techniques. The pitch of adjacent turns of coil 136 may be tightly wrapped so that each turn touches the succeeding turn, or the pitch may be set such that coil 136 is wrapped in an open fashion. Moreover, the pitch of the coil can be varied along the length device 10. In some embodiments, a coating, for example a lubricious (e.g., hydrophylic) or other type of coating, may be applied over portions or all of coil 136. Some examples of such coatings include those discussed below with regard to coatings that can be used on the support member 12. Additionally, the thickness of the coil may be varied along the longitudinal axis of the device 10.

Coil 136 may include a proximal end that is coupled to or otherwise attached to shaft 10. The coil 136 can be attached using suitable attachment mechanism, for example a solder joint or other suitable attachment means such as adhesives, thermal bonding, mechanical bonding, and the like. A distal end of coil 136 may be coupled to shaft 10, for example, by a distal solder ball tip or other suitable connection. It is also of note that in embodiments where device 134 is a guidewire, device 134 may include some of the other structural features of guidewires. For example, device 134 may include a proximal connector.

In order to incorporate other desirable properties into device 134, for example, improve distal flexibility, coil 136 may taper inward toward shaft 10. For example, coil 136 may define the outside diameter of a portion of device 134, and the outside diameter may be greater near the proximal end of coil than at the distal end of coil 136.

Shaft construction details have been described in particular to wires used to make guidewires. However, the methods described are equally applicable to any medical device incorporating an elongate shaft for which stringent specifications are required for straightness and profile. Exemplary uses would include a wire used as a core wire in a balloon catheter or a wire used to form a stylet for a catheter or introducer.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of processing an elongate shaft, the method comprising:
   providing an elongate shaft having a twist orientation;
   providing a grinding apparatus having a spin configuration that is aligned in the same direction as the twist orientation; and
   grinding at least a portion of the shaft with the grinding apparatus.

2. The method of claim 1, wherein the shaft has a left-hand twist orientation.

3. The method of claim 1, wherein the shaft has a right-hand twist orientation.

4. The method of claim 1, wherein the grinding apparatus includes a rotatable work wheel and an infeed rail.

5. The method of claim 4, wherein the shaft is slidably and rotatably disposed on the infeed rail.

6. The method of claim 5, wherein the work wheel rotates in a first direction and wherein the shaft rotates in a second direction that is dependent on the first direction, and wherein the spin orientation is defined by the combination of the rotation of the work wheel and the rotation of the shaft.

7. A method of manufacturing a guidewire, the method comprising:
   providing an elongate shaft having a twist orientation;
   providing a grinding apparatus having a spin configuration that is aligned in the same direction as the twist orientation;
   grinding at least a portion of the shaft with the grinding apparatus; and
   disposing an outer member over a region of the shaft.

8. The method of claim 7, wherein the shaft has a left-handed twist orientation.

9. The method of claim 7, wherein the shaft has a right-handed twist orientation.

10. The method of claim 7, wherein the step of providing an elongate shaft having a twist orientation includes twist straightening the shaft to create a groove along the length of the shaft that defines the twist orientation.

11. A method of processing an elongate shaft, the method comprising:
   providing the elongate shaft having a twist orientation;
   providing a means for grinding the elongate shaft in the same direction as the twist orientation; and
   grinding at least a portion of the shaft with the means for grinding.

* * * * *